US009668691B2

(12) United States Patent
Korichi et al.

(10) Patent No.: US 9,668,691 B2
(45) Date of Patent: Jun. 6, 2017

(54) METHOD TO MEASURE SKIN ELASTICITY AND FIRMNESS

(71) Applicant: LVMH RECHERCHE, Saint Jean de Braye (FR)

(72) Inventors: Rodolphe Korichi, Saint Jean de Blanc (FR); Marie Baret, Boulogne Billancourt (FR); Delphine Pelle De Queral, Ingres (FR); Germaine Gazzano, Levallois-Perret (FR)

(73) Assignee: LVMH RECHERCHE, Saint Jean de Braye (FR)

( * ) Notice: Subject to any disclaimer, the term of this patent is extended or adjusted under 35 U.S.C. 154(b) by 0 days.

(21) Appl. No.: 13/624,115

(22) Filed: Sep. 21, 2012

(65) Prior Publication Data

US 2013/0079643 A1    Mar. 28, 2013

Related U.S. Application Data (60) Provisional application No. 61/537,891, filed on Sep. 22, 2011.

(51) Int. Cl.
*A61B 5/00* (2006.01)
*A61B 5/01* (2006.01)

(52) U.S. Cl.
CPC .......... *A61B 5/442* (2013.01); *A61B 5/0053* (2013.01); *A61B 5/0082* (2013.01); *A61B 5/01* (2013.01); *A61B 5/0077* (2013.01)

(58) Field of Classification Search
CPC ...... A61B 5/442; A61B 5/0082; A61B 5/0053
USPC ....................................................... 600/474
See application file for complete search history.

(56) References Cited

U.S. PATENT DOCUMENTS

| 4,888,342 | A | * | 12/1989 | Kligman | 514/419 |
| 5,587,396 | A | * | 12/1996 | Smith | 514/557 |
| 2003/0005781 | A1 | * | 1/2003 | Oba | A61B 5/0053 73/862.381 |
| 2008/0077053 | A1 | * | 3/2008 | Epstein | A61B 5/0053 600/591 |
| 2008/0200842 | A1 | * | 8/2008 | Lim | A61B 5/0053 600/587 |
| 2008/0234607 | A1 | * | 9/2008 | Hunter-Jones | A61B 5/442 600/587 |
| 2009/0175408 | A1 | * | 7/2009 | Goodsitt et al. | 378/37 |
| 2010/0286493 | A1 | * | 11/2010 | Duncan | A61B 5/442 600/306 |

(Continued)

OTHER PUBLICATIONS

Murray et al.: "Correlations between Dermal Torque Meter®, Custometer®, and Dermal Phase Meter® measurements of human skin"; Skin Research and Technology 1997, 3, pp. 101-106.

(Continued)

*Primary Examiner* — Rajeev Siripurapu
(74) *Attorney, Agent, or Firm* — Hamre, Schumann, Mueller & Larson, P.C.

(57) ABSTRACT

The invention relates to a method of measuring the elasticity and firmness of skin. The invention also relates to methods of measuring improvements in a person's skin health by measuring firmness and elasticity before, during and after a cosmetic treatment. The invention further relates to methods of measuring the improvement in a person's skin firmness and elasticity that a cosmetic agent may cause when applied on the skin.

9 Claims, 5 Drawing Sheets

(56) References Cited

U.S. PATENT DOCUMENTS

2010/0291250 A1* 11/2010 Paufique .................. 424/779
2011/0212146 A1* 9/2011 Helland et al. ............ 424/401

OTHER PUBLICATIONS

Barel et al.: "Suction Method for Measurement of Skin Mechanical Properties: The Cutometer®"; Handbook of Non-Invasive Methods and the Skin, Chapter 14.3 (1995) pp. 335-340.

Jemec et al.: "Measurement of the mechanical properties of skin with ballistometer and suction cup"; Skin Research and Technology 2001, 7, pp. 122-126.

Paye et al.: "Use of the Reviscometer® for measuring cosmetics-induced skin surface effects"; Skin Research and Technology 2007, 13, pp. 343-349.

Bazin et al.: "Skin Aging Atlas: Caucasian type, vol. 1"; Med'Com 2007, pp. 46-57.

Sheffield et al.: "A Comparison of Body-Image Dissatisfaction and Eating Disturbance among Australian and Hong Kong Women", European Eating Disorders Review, 13, pp. 112-124 (2005).

Tiggemann et al.: "Body Image Across the Life Span in Adult Women: The Role of Self-Objectification", Development Phycology, 2001, vol. 37, No. 2, pp. 243-253.

Leiblum et al.: "Sexualilty and the Midlife Woman"; Psychology of Women Quarterly, 14 (1990), pp. 495-508.

Tsukahara et al.: "Determination of age-related changes in the morphological structure (sagging) of the human cheek using a photonumeric scale and three-dimensional surface parameters", International Journal of Cosmetic Science, 22, pp. 247-258 (2000).

Ezure et al.: "Sagging of the cheek is related to skin elasticity, fat mass and mimetic muscle function", Skin Research and Technology 2009, 15, pp. 299-305.

Ryu et al.: "Influence of age and regional differences on skin elasticity as measured by Cutometer®"; Skin Research and Technology 2008, 14, pp. 354-358.

Kapoor et al.: "Age Dependent Studies as Various Skin Parameters Using Cutometer"; Indian J. Pharm. Educ. Res. 43(4), Oct.-Dec. 2009, pp. 338-345.

\* cited by examiner

METHOD TO MEASURE SKIN ELASTICITY AND FIRMNESS

RELATED APPLICATIONS

This application claims priority to and benefit of U.S. Provisional Application No. 61/537,891, entitled Method to measure skin elasticity by Rodolphe Korichi et. al. filed Sep. 22, 2011.

FIELD OF THE INVENTION

The invention relates to a method of measuring the elasticity and firmness of skin. The invention also relates to methods of measuring improvements in a person's skin health by measuring firmness and elasticity before, during and after a cosmetic treatment. The invention further relates to methods of measuring the improvement in a person's skin firmness and elasticity that a cosmetic agent may cause when applied on the skin.

BACKGROUND OF THE INVENTION

For several years, cosmetic products have been developed having rheological action on the skin, such as firmness, tonicity, elasticity or suppleness. The measurement of the efficacy thereof has for many years been assessed from different scientific angles such as clinical and instrumental approaches.

As far as women are concerned, numerous visual and sensory criteria are involved in the subjective phenomenon of skin firmness and elasticity.

For some, evaluation of skin texture is primarily indicative of firmness whilst others palpate their skin beneath their fingertips to assess its resistance or density. Some women will actually evaluate tissue firmness by looking at themselves in a mirror. Although all of these factors interact with each other, touch and sensation are still the two parameters most widely used to evaluate perceived firmness and elasticity. Furthermore, the dermatologist's specific and standardised approach towards clinical evaluation and skin sagging is based primarily on pinching the skin between two fingers.

From the instrument standpoint, some validated methods propose various ways of deforming the skin such as suction, twisting or stream of pressurized air. However, a frequent disadvantage associated with these methods is that the deformity is often limited to a small surface area of skin, which differs from the area assessed by women and/or the experts in their evaluation.

Thus the "firmness" perception includes many aspects that prior art approaches cannot significantly characterize in a whole. Another problem to be faced is that principal measuring techniques focus on the analysis of small skin surface areas and therefore lack a reliant correlation with the clinical evaluations.

To be closer in line with clinical evaluation of skin firmness as conducted both i) by individual on their sensed and perceived viscoelastic properties of the skin and ii) by dermatologists, the inventors have developed a novel quantitative approach combining both infrared thermography imaging and a skin pinching system.

The present invention intends to obtain more descriptive and quantitative data on perceived elasticity and other rheological properties such as firmness and tonicity.

In order to get information closer to consumers' perception, the present inventors have developed a new method using skin deformation system and infrared thermography imaging.

SUMMARY OF THE INVENTION

The present invention deals with a method that uses infrared thermography in combination to a mechanical deformation system. The method of the invention is relevant in characterizing the perceptual phenomenon of skin elasticity and firmness. The inventors have found an excellent correlation of the method with the volunteers' subjective assessment of their skin's elasticity.

A further embodiment of the invention comprises the steps of comparing an elasticity value to a database of known elasticity values, and determining a theoretical age of the skin of the individual.

Another embodiment of the method includes steps for determining the effect of a cosmetic agent; comparison is conducted prior to and then after treatment with a topically or orally administered agent for improving skin health.

DETAILED DESCRIPTION OF THE INVENTION

The subject of the present invention is a novel instrumental method using infrared thermography imaging coupled with a mechanical deformation system of the skin. This method is useful for characterizing rheological properties of the skin.

According to one of its aspects, the invention deals with a method of determining a skin elasticity value for the skin of an individual, said method using infrared thermography imaging coupled with a mechanical deformation system comprising at least two metallic plates intended to pinch a skin sample of a person.

In a preferred embodiment, the method deals with determining the elasticity of skin face. In this embodiment, "Elasticity" as used in the context of the present invention may correspond to one or several clinical criteria such as firmness, tonicity, suppleness, sagging skin, oval of the face, bags beneath the eyes, nasolabial folds or ptosis of the lower part of the face. Such clinical criteria are usually estimated by the person him/herself, or by a dermatologist. They can be defined for example by using a graduated, validated, visual scale such as one described in Bazin, R., Doublet, E., In: MED'COM (Eds), Skin Aging Atlas, Volume 1 Caucasian Type, Paris, France, 2007, pp: 46-57.

The volunteers' self-assessment was specifically quantified by the method of the invention, particularly as regards firmness, elasticity and skin sagging. The method of the invention is an interesting alternative to current subjective methods and enables to quantify the rheological properties of the skin. The method of the invention resolves the difficulty of measuring the subjective perception of the global phenomenon of skin firmness, elasticity and sagging. The inventors showed that the measurement performed with the method of the invention were consistent with the volunteers' subjective assessment of their skin's elasticity.

According one embodiment, the method comprises the steps of
- a—contacting the metallic plates of the mechanical deformation system with the skin sample and recording a first thermal image of the skin on which thermal prints of the metallic plates on skin can be displayed,
- b—pinching the skin sample with the mechanical deformation system intended to trap said skin sample, and subsequently releasing the system,
- c—recording a second thermal image of the skin on which thermal prints of the metallic plates on skin can be displayed,
- d—calculating a value associated with an elastic recovery of the skin sample.

In step b, the pinching of the skin is preferably made under a controlled pressure being between 20 and 40 N, more preferably between 25 and 35 N, typically being 31 N.

The metallic plates are preferably parallel so that contact between the metallic plates with the skin generates parallel markings displayed with infrared thermography imaging.

The value associated with an elastic recovery of the skin sample corresponds to the ratio between a first distance corresponding to the distance between the thermal prints of the metallic plates measured after pinching in step c, and a second distance corresponding to the distance between the thermal prints of the metallic plates measured before pinching in step a.

A visual reproduction of the deformation can be obtained using infrared thermography imaging ThermaCAM™ SC500PAL camera, FLIR System™, Sweden. Once the system is removed from the skin after application, a thermal image of the face is usually recorded. The contact between the system's metallic bars (cold temperature) with the skin (warm temperature) generates clearly discernible markings. The distance (in cm) from the centre of each of the marks left on the skin is calculated. The same distance is also measured before pinching.

To evidence rheological variations, the measurements of the distance separating the two imprints left by the system in the image are taken before (AV) and immediately after the restriction (AP), and the ratio of both distances $R = AP/AV$ distance is calculated. This calculation can be made either manually by experts or using software.

The closer this ratio is to the value of 1, the greater the rheological properties of the skin (increased elasticity and suppleness). If this ratio is low, the skin has reduced elasticity and suppleness.

Figure 1:
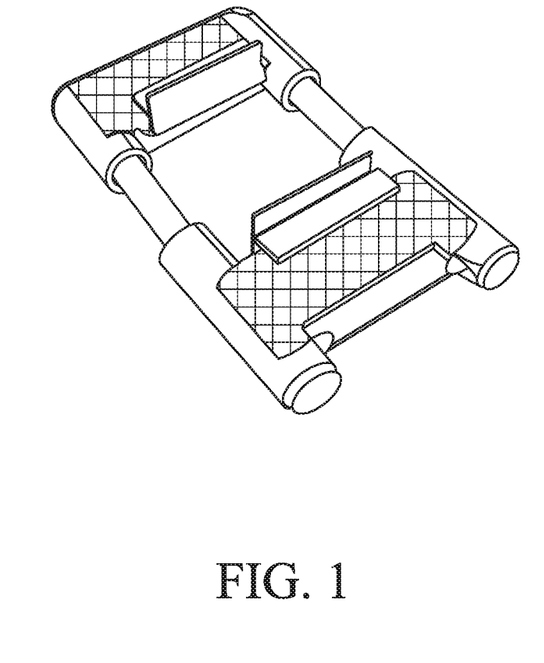
FIG. 1 represents a pinching system that can be used according to the present invention.

In one embodiment, the pinching system is formed by an internal spring and two metallic plates fixed to two sliding sections (FIG. 1).

The two sections slide under a constant, controlled pressure of between 20 and 40, for example 31 N. To carry out measurements, the pinching system is placed at certain points of the skin surface in static position to set up contact with the metallic plates of the system. Then, using the fingers, the two outer parts of the system are pulled inwards as far as an abutment thus trapping part of the skin within the created space. The system is then relaxed to release the skin allowing it to return to its initial state.

The mechanical deformation system can be placed at certain points of the skin surface in static position to set up contact with the metallic plates of the system.

The method of the invention is preferably conducted on the face, more preferably on the lower part of the cheek.

According to another aspect, the invention deals with a method of measuring the impact of various cosmetic products on improving the subjective perception of firmness.

One object of the invention is a method for measuring the effect of a cosmetic product on improving the firmness or elasticity of the skin of a person, said method comprising:
- calculating a first value associated with an elastic recovery of the skin sample according to the method of determining a skin elasticity value previously described,
- applying the cosmetic product on the skin sample,
- calculating a second value associated with an elastic recovery of the skin sample according to the method of determining a skin elasticity value previously,
- comparing the first value and the second value.

The invention is illustrated more in detail in reference to the following examples.

Example 1: Instrumental Evaluation According to the Invention and Correlation with Clinical Assessment 116 Caucasian women, allocated to 5 different age groups (group "20-29", n=20, mean=24.3+/−3.1 years; group "30-39", n=23, mean=34.4+/−2.8 years; group "40-49", n=23, mean=44.4+/−3.0 years; group "50-59", n=24, mean=54+/−3.1 years and the group "60-70", n=26, mean=64.9+7−3.4 years), were recruited for this study.

A—Instrumental Evaluation According to the Invention

Study Protocol

The volunteers were invited to sit down in a comfortable armchair in order to prevent any head movements during measurement. An infrared thermography camera set up a fixed distance away from the volunteer, was used to capture the image of the skin before and after mechanical deformation.

Pinching System

Figure 2:
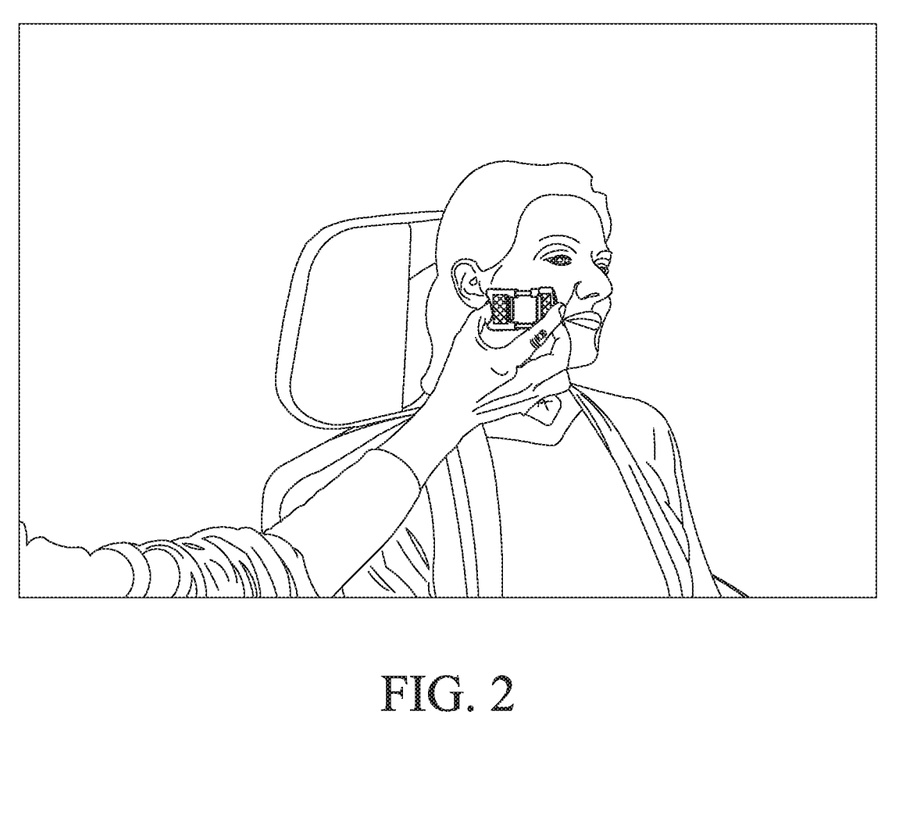
FIG. 2 gives an example of the positioning of the pinching system on the cheek. Skin is trapped between the two metallic parts of the pinching apparatus.
Figure 4:
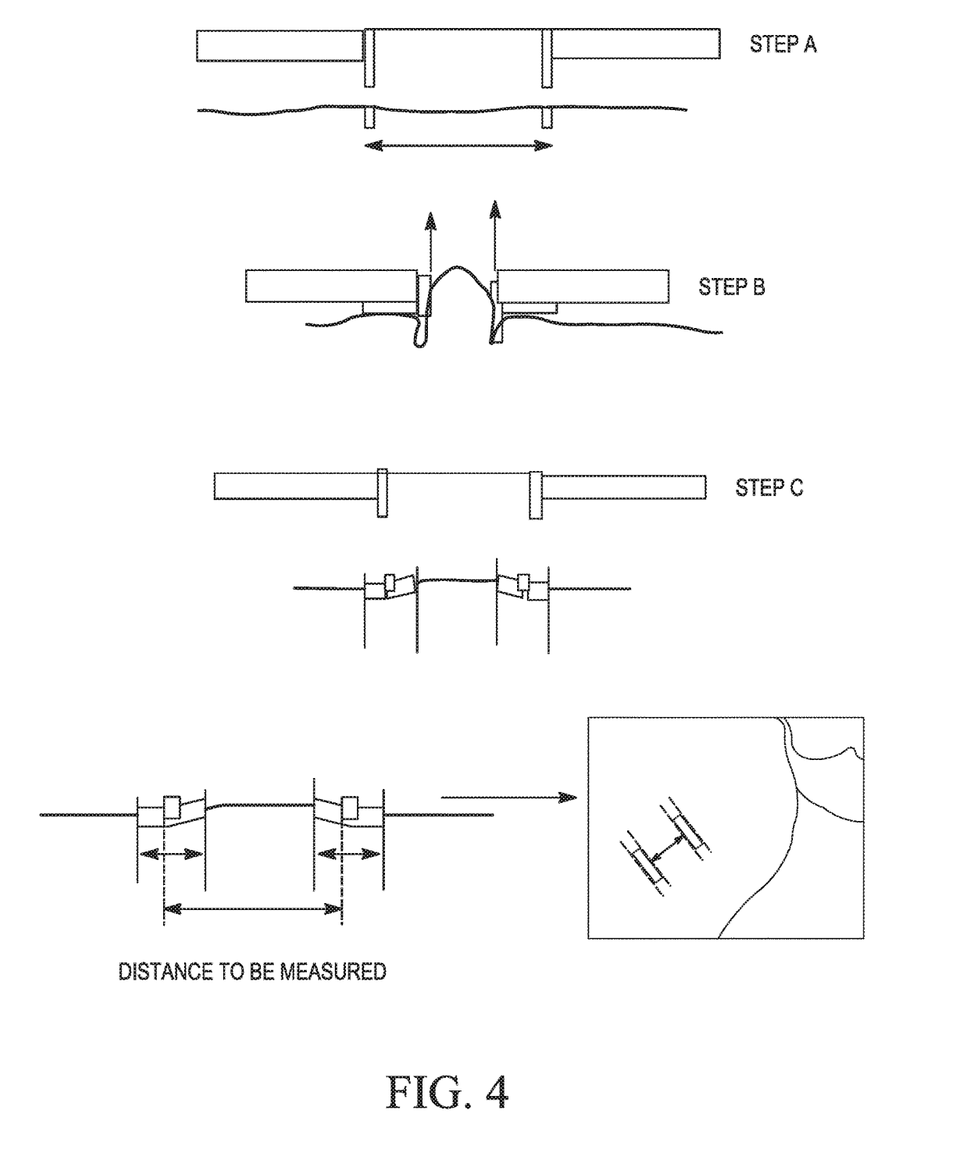
FIG. 4 gives the description of the different skin pinching steps:
Step a: Positioning of the system
Step b: Pinching of the skin
Step c: Stop pinching the skin by releasing the system.

A system comprising an internal spring and 2 metallic plates fixed to 2 sliding sections was used for this study (see FIG. 1). To record the measurement, the pinching system was placed on the skin in a static position in order to create contact between the system's metallic plates and the skin. Then, using the fingers, the two outer parts of the system were pulled inwards as far as the wedge (the two sections slide at a controlled constant pressure of 31 N), thus trapping part of the skin within the space created (see FIG. 2). Finally, the two sections were relaxed thus releasing the skin and allowing it to return to its initial state (see FIG. 4).

Infrared Thermography

Skin deformation was analysed using an infrared thermography camera (ThermaCAM™ SC500PAL, FLIR SYSTEM™, Sweden).

Figure 3:
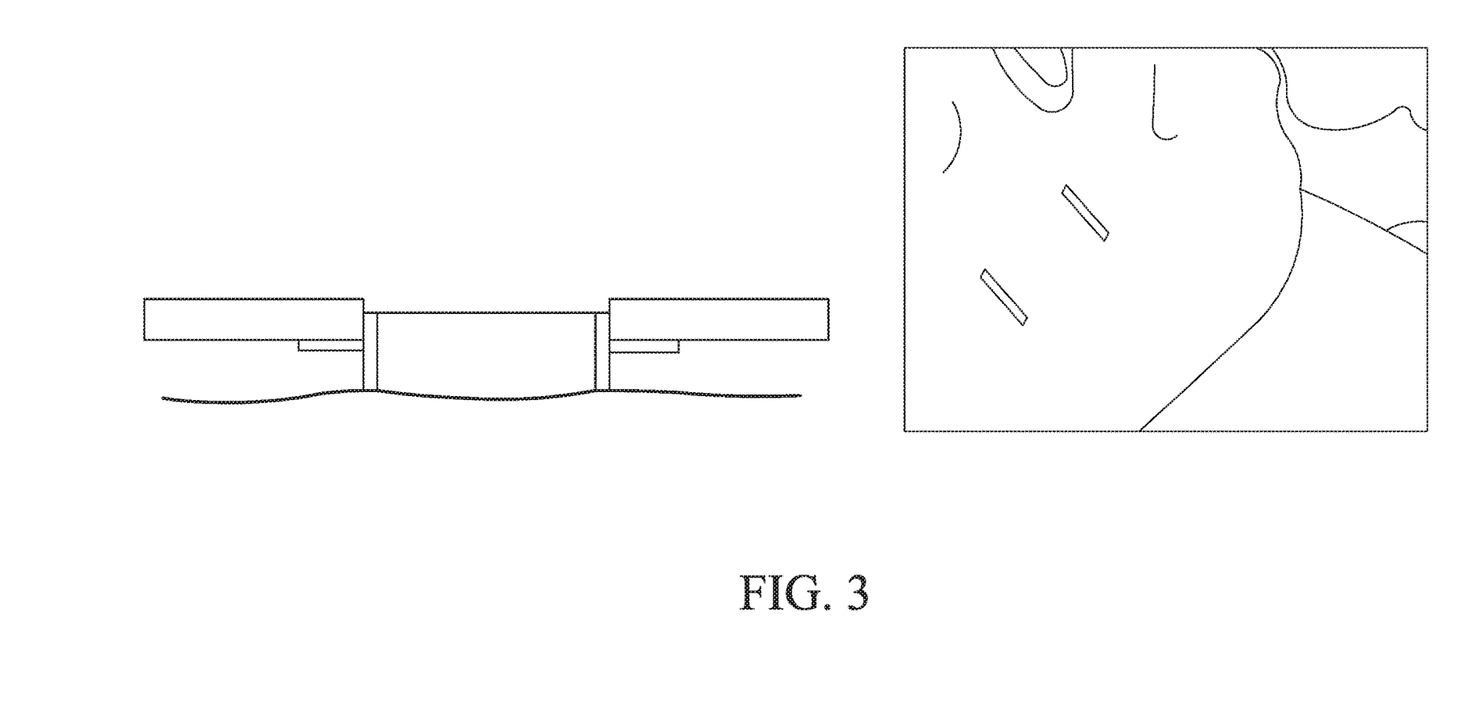
FIG. 3 is an image of the face obtained by infrared thermography, once the metallic parts of the pinching system has been placed on the surface of the skin face before pinching.

A first thermal image was recorded before pinching (see FIG. 3).

The contact between the system's metallic bars (cold temperature) with the skin (warm temperature) generates clearly discernible vertical and parallel markings. The distance (in cm) from the centre of each of the marks left on the skin is calculated.

Once the system was removed from the skin after application after pinching, a second thermal image was recorded.

The distance separating the two vertical prints on the image is measured before (AV) and immediately after (AP) the restriction and the ratio of both distances (R=distance AP/distance AV) is calculated.

Two way analysis of variance (ANOVA) and linear regression were used to assess the effect of age. The correlations were studied on the basis of linear regression (two by two) and Principal Component Analysis (PCA). All of the statistical tests were analysed with a risk $\alpha=5\%$.

Repeatability and Reproducibility of the Method

A study was conducted to verify the repeatability and reproducibility of the measurements. Three experts quantified the distances before and after pinching of the skin. Four photos were taken by panellists: 2 photos before pinching and 2 photos after pinching.

The results clearly show that the measurements are fully repeatable and reproducible (see the Table I below).

TABLE I

Repeatability and reproducibility of the method

| | Nominal values | Mean variations (Sr) | Maximum variations (r) |
|---|---|---|---|
| Distance BEFORE pinching AV (cm) | 2.62 | ±0.05 | ±0.14 |
| Distance AFTER pinching AP (cm) | 2.02 | ±0.07 | ±0.9 |

B—Results According Age Groups

Figure 5:
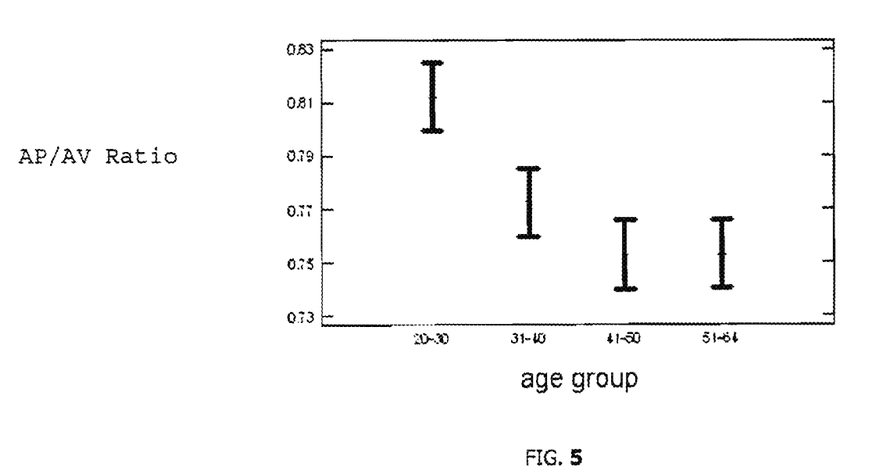
FIG. 5 represents the trend in the AP/AV distance ratio as a mean of 3 experts' estimation, as a function of age.

The older the person, the more the rheological AP/AV index is reduced. The reduction of AP/AV index goes along with the loss of the skin's rheological characteristics (suppleness, elasticity) (see Table II and FIG. 5).

TABLE II

AP/AV ratios according to age groups

| | 20-30 | 30-40 | 40-50 | 50-60 | Signif. |
|---|---|---|---|---|---|
| Expert 1 | 0.84 | 0.80 | 0.76 | 0.77 | S (<0.01) |
| Expert 2 | 0.81 | 0.77 | 0.75 | 0.75 | S (<0.01) |
| Expert 3 | 0.79 | 0.76 | 0.75 | 0.74 | S (<0.01) |

Statistical analysis of the AP/AV distance ratio revealed a significant age-related correlation ($r=-0.23$, $p=0.02$).

C-Study on the Correlation of the AP/AV Index with Subjective Evaluation of Rheological Criteria The coherency between the measurements taken using the method of the invention (pinching combined with infrared thermography) and a subjective evaluation previously carried out has been verified.

Volunteers' Self-Assessment and Clinical Evaluation

Each volunteer was asked, in front of a mirror, to answer the self-assessment questionnaire (based on the information collected during the interviews), scoring each item on a scale of 1 to 10 (1 being the lowest score and 10 being the highest). All of the evaluations were carried out on skin without cream and make-up. Some of the evaluations were carried out in front of the mirror in order to record the extent of sagging skin in three areas using a graduated, validated, visual scale as described in Bazin, R., Doublet, E., In: MED'COM (Eds), Skin Aging Atlas, Volume 1 Caucasian Type, Paris, France, 2007, pp: 46-57, such as bags under the eyes, nasolabial folds and ptosis of the lower part of the face. A zero score denoted no visible presence of sagging whilst 10 indicated the highest level of sagging.

The results are summarized in the Table below.

TABLE III

Volunteers' self-assessment

| | Group "20-29" | Group "30-39" | Group "40-49" | Group "50-59" | Group "60-70" | P value |
|---|---|---|---|---|---|---|
| FIRMNESS «F» | 7.5 $^A$ | 6.6 $^B$ | 6 $^{BC}$ | 5.3 $^C$ | 5.3 $^C$ | S (p < 0.01) |
| ELASTICITY «E» | 7.6 $^A$ | 6.6 $^B$ | 6.5 $^B$ | 5.4 $^C$ | 5.3 $^C$ | S (p < 0.01) |
| SMOOTH APPEARANCE OF THE SKIN | 6.6 | 6.3 | 6.1 | 6.3 | 6.7 | NS |
| MOISTURE PERCEPTION | 5.4 | 5.2 | 5.7 | 5.3 | 5.3 | NS |
| SAGGING SKIN «SS» | 1.1 $^A$ | 2.9 $^B$ | 4 $^C$ | 4.8 $^D$ | 5.3 $^D$ | S (p < 0.01) |
| OVAL OF THE FACE | 8.7 $^A$ | 7.3 $^A$ | 6.3 $^B$ | 5.2 $^B$ | 5.2 $^C$ | S (p < 0.01) |
| FINE LINES | 2.2 $^A$ | 4.6 $^B$ | 5.2 $^{BC}$ | 6.4 $^{CD}$ | 6.2 $^D$ | S (p < 0.01) |
| WRINKLES | 1.4 $^A$ | 3.5 $^B$ | 5.3 $^C$ | 6 $^{CD}$ | 6.5 $^D$ | S (p < 0.01) |
| BAGS BENEATH THE EYES | 0.7 $^A$ | 1.4 $^A$ | 1.7 $^A$ | 2.7 $^B$ | 2.8 $^B$ | S (p < 0.01) |
| NASOLABIAL FOLDS | 0.7 $^A$ | 0.9 $^B$ | 2 $^C$ | 3.3 $^C$ | 3.5 $^C$ | S (p < 0.01) |
| PTOSIS OF THE LOWER PART OF THE FACE | 0.4 $^A$ | 1.8 $^B$ | 2.9 $^C$ | 3.1 $^D$ | 3.5 $^D$ | S (p < 0.01) |

Note:

When there are significant differences between age groups for each item, letters indicate the age groups to which it belongs. If the groups have the same letter, they are comparable, if not they are they significantly different.

The results have shown a marked reduction in the firmness, elasticity and oval of the face with age. Increased sagging of the skin is also clearly apparent with advancing age. As regards the analysis of the various visual grades, the results have shown a significant increase in value for the three facial areas studied (bags beneath the eyes, nasolabial folds and oval structure of the face). At the same time, fine lines and wrinkles are logically accentuated with age.

A clinical evaluation was carried out by a dermatologist at the same time as the subjective self-evaluation. The same items than the ones listed in the self-assessment questionnaire, and the same visual scales for skin sagging were used for the clinical evaluation.

The results of the clinical evaluation were very similar to those of the self-assessment except for perceived moisture levels, which fell significantly with age.

Correlation of the AP/AV Index with Subjective Evaluation of Rheological Criteria Overall, the results clearly showed that the AP/AV ratio gives a coherent description of the subjective assessment made by women on the elasticity and firmness of their skin.

Data analysis emphasized significant links with the volunteers' self-assessment for certain items and according to age ("Firmness F": $r=0.32$, $p<0.01$; "Elasticity E": $r=0.28$, $p<0.01$; "Sagging skin SS": $r=0.37$, $p<0.01$).

Example 2: Study on the Efficacy of a Cosmetic Product

A study on the efficacy of a cosmetic product was conducted over a period of 3 weeks in France in 40 individuals. The measurements were made on nude skin before and after 3 weeks' treatment. The treatment consisted in a twice-a-week application for 3 weeks of a product marketed under the trade name Masque Revitalisant—Dior Prestige de Christian Dior (mask in fabric).

The AP/AV ratio was measured in the same conditions as described in Example 1. The results are reproduced in Table IV.

Under the study conditions, the treatment allowed a significant improvement in the suppleness/elasticity of the skin as expressed by a significant increase in the AP/AV ratio.

TABLE IV

AP/AV ratio before and after a cosmetic treatment

|  | T0<br>Before application<br>(nude skin) | T1<br>After 3 weeks use<br>(nude skin) | P* time |
|---|---|---|---|
| AP/AV ratio | 0.745 | 0.764 | S (<0.01) |

P* time was calculated with a risk of $\alpha = 5\%$

What is claimed is:

1. A method of determining a skin elasticity value for a person's skin, comprising:
   (a)—contacting two parallel metallic plates of a mechanical pinching system on a skin surface zone, recording a first thermal image of the skin surface zone that displays thermal prints of the metallic plates on skin with an infrared thermography imaging apparatus, and measuring a first distance between the two parallel metallic plates on the first thermal image,
   (b)—after the recording of the first thermal image, pushing at least one of the two parallel metallic plates of the mechanical deformation system toward the other in a direction that is parallel to the skin surface, so as to pinch the skin between the two parallel metallic plates, under a controlled pressure, wherein the two parallel metallic plates remain parallel during the pushing,
   (c)—releasing the controlled pressure,
   (d)—after releasing the controlled pressure, recording a second thermal image of the skin surface zone that displays thermal prints of the metallic plates on skin with the infrared thermography imaging apparatus, and measuring a second distance between the two parallel metallic plates on the second thermal image, and
   (e)—determining a skin elasticity value associated with an elastic recovery of the skin, said skin elasticity value corresponding to the ratio between the second distance and the first distance.

2. The method of claim 1, wherein in (b), the controlled pressure is between 20 and 40 N.

3. The method of claim 2, wherein the skin is considered as having elasticity when the skin elasticity value is higher than 1.

4. The method of claim 1, wherein the mechanical deformation system comprises an internal spring and two metallic plates attached to two sliding sections.

5. A method for measuring the effect of a cosmetic product on improving the firmness or elasticity of a person's skin, said method comprising:
   calculating a first value associated with an elastic recovery of the skin sample according to the method of claim 1,
   applying the cosmetic product on the skin sample,
   calculating a second value associated with an elastic recovery of the skin sample according to the method of claim 1, and
   comparing the first value and the second value.

6. The method of claim 1, wherein the skin elasticity value corresponds to at least one of determining firmness, tonicity, suppleness, sagging skin, oval of the person's face, bags beneath the person's eyes, nasolabial folds or ptosis of the lower part of the person's face.

7. The method of claim 1, wherein the method is conducted on skin of the person's face.

8. The method claim 1, wherein the method is conducted on a lower part of the person's cheek.

9. The method of claim 1, wherein the pushing of the at least one of the two parallel metallic plates toward the other narrows a space between the two parallel metallic plates; and
   deforms the pinched skin within the space between the two parallel metallic plates;
   wherein upon releasing the pressure, the pinched skin returns to an unpinched position.

* * * * *